(12) United States Patent
Gill

(10) Patent No.: US 8,768,439 B2
(45) Date of Patent: Jul. 1, 2014

(54) PHYSIOLOGICAL MONITORING USING AN OCULAR PROBING SYSTEM AND METHOD

(75) Inventor: Douglas M. Gill, South Orange, NJ (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/568,804

(22) Filed: Aug. 7, 2012

(65) Prior Publication Data

US 2014/0046151 A1    Feb. 13, 2014

(51) Int. Cl.
   *A61B 3/10*      (2006.01)
   *A61B 3/11*      (2006.01)

(52) U.S. Cl.
   USPC ............................................ 600/476; 351/219

(58) Field of Classification Search
   USPC ................................... 351/219; 356/478
   See application file for complete search history.

(56) References Cited

U.S. PATENT DOCUMENTS

| | | | | |
|---|---|---|---|---|
| 4,007,980 | A * | 2/1977 | Bracher et al. | 351/219 |
| 4,169,664 | A * | 10/1979 | Bailey, Jr. | 351/226 |
| 4,485,820 | A * | 12/1984 | Flower | 600/320 |
| 5,297,554 | A | 3/1994 | Glynn et al. | |
| 6,654,528 | B2 | 11/2003 | Rosenast | |
| 6,746,400 | B2 | 6/2004 | Rathjen | |
| 7,137,952 | B2 | 11/2006 | Leonardi et al. | |
| 7,283,692 | B2 * | 10/2007 | Xiao et al. | 385/12 |
| 7,403,805 | B2 | 7/2008 | Abreu | |
| 7,697,121 | B1 * | 4/2010 | Coroy et al. | 356/35.5 |
| 7,809,417 | B2 | 10/2010 | Abreu | |
| 2007/0191695 | A1 | 8/2007 | Abrams et al. | |
| 2007/0270673 | A1 | 11/2007 | Abrams et al. | |
| 2008/0218696 | A1 | 9/2008 | Mir | |
| 2010/0113901 | A1 | 5/2010 | Zhang et al. | |

FOREIGN PATENT DOCUMENTS

JP            20115261 A       1/2011

OTHER PUBLICATIONS

Mengual et al., "Optical phase-based beamformer using MZM SSB modulation combined with crystal polarization optics and a spatial light modulator". Optics Communications 281 (2008). pp. 217-224.*
Wiederhecker et al., "Field enhancement within an optical fibre with a subwavelength air core". Nature Photonics. vol. 1., 2007. pp. 115-118.*
Thomas. "The Differential Diagnosis of Fixed Dilated Puplis: A Case Report and Review". Critical Care and Resuscitation. 2000; 2: 34-37.*
Wavering. "Optical Path Length Multiplexing of Optical Fiber Sensor". Virginia Polytechnic Institute and State University. 1998.*

(Continued)

*Primary Examiner* — Long V. Le
*Assistant Examiner* — Colin T Sakamoto
(74) *Attorney, Agent, or Firm* — Cantor Colburn LLP; Vazken Alexanian

(57) ABSTRACT

A method and system perform physiological monitoring. The system includes a first light source and a plurality of optical waveguide couplers, each of the plurality of optical waveguide couplers being arranged at a different predetermined spatial location on an ocular insert to be placed on an eye. The system also includes a plurality of optical waveguides. Each optical waveguide carries light from a second light source to a respective one of the plurality of optical waveguide couplers and carries a received signal from the respective one of the plurality of optical waveguide couplers. A processor receives the received signal from each of the plurality of optical waveguides and monitors a parameter based on the received signal.

18 Claims, 6 Drawing Sheets

(56) References Cited

OTHER PUBLICATIONS

Info Cellar. "Wave Division Multiplexing". archived by WayBack Machine Jul. 13, 2004. retrived <http://web.archive.org/web/20040713013548/http://www.infocellar.com/networks/fiber-optics/wdm.htm>.*

Tumlinson et al., "Miniature endoscope for simultaneous optical coherence tomography and laser-induced fluorescence measurement". Applied Optics. vol. 43, No. 1, 2004. pp. 113-121.*

* cited by examiner

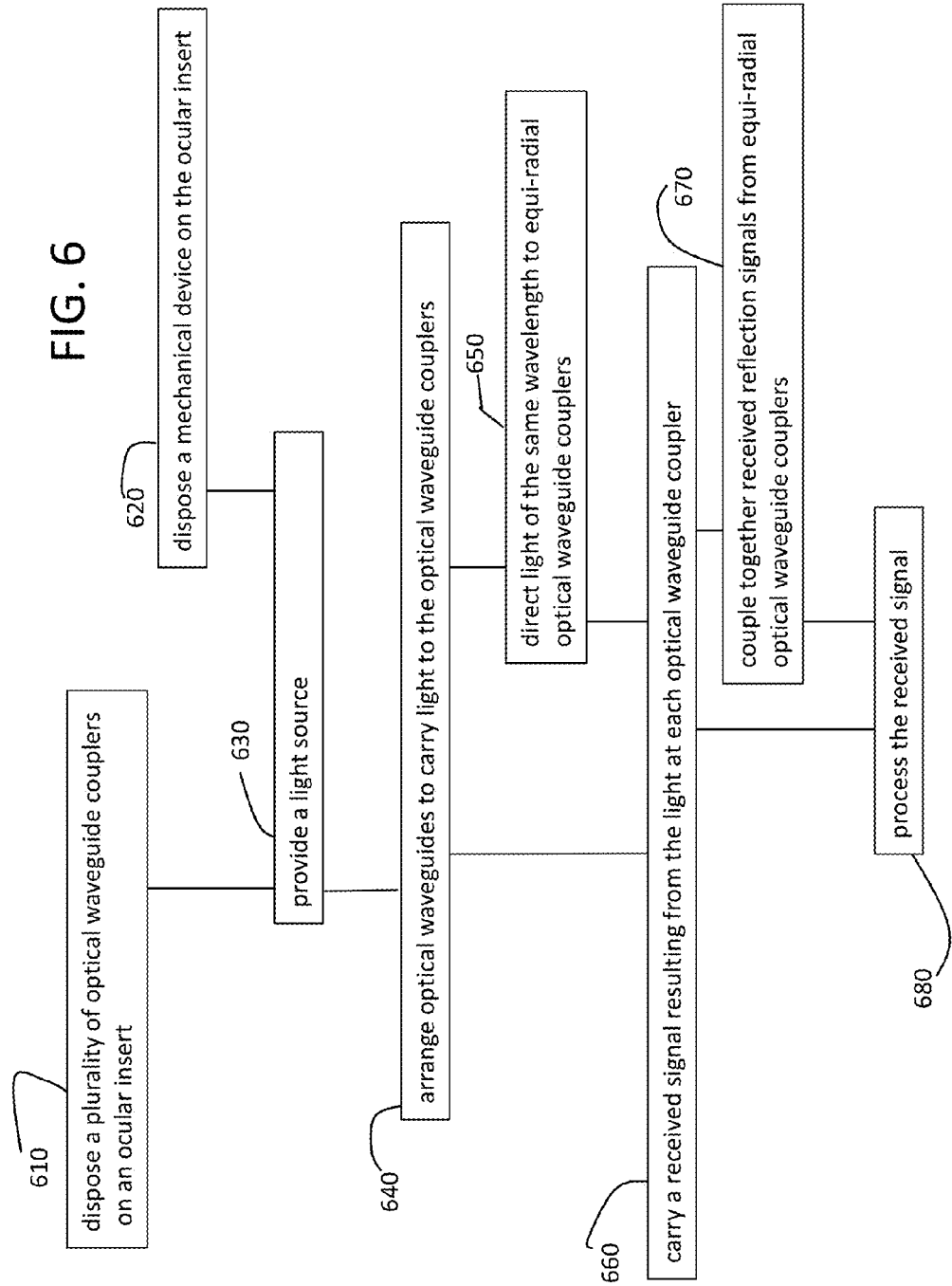

PHYSIOLOGICAL MONITORING USING AN OCULAR PROBING SYSTEM AND METHOD

BACKGROUND

The present invention relates to physiological monitoring, and more specifically, to ocular probing.

Patient monitoring is critical during and after a medical procedure. For example, an unconscious or comatose patient's neurological status may be monitored by periodically opening his or her eyes, shining a light into the eyes, and noting the constriction and subsequent dilation of the pupils. However, these types of monitoring procedures do not provide a real time or necessarily even a complete profile of the patient's well-being. Thus, improved monitoring techniques would be appreciated in the health care industry.

SUMMARY

According to one embodiment, a physiological monitoring system includes a first light source; a plurality of optical waveguide couplers, each of the plurality of optical waveguide couplers being arranged at a different predetermined spatial location on an ocular insert to be placed on an eye; a plurality of optical waveguides, each optical waveguide carrying light from a second light source to a respective one of the plurality of optical waveguide couplers and carrying a received signal from the respective one of the plurality of optical waveguide couplers; and a processor configured to receive the received signal from each of the plurality of optical waveguides and to monitor a parameter based on the received signal.

According to another embodiment, a physiological monitoring method includes disposing a plurality of optical waveguide couplers on an ocular insert configured to cover an eye; providing a light source to be carried to each of the plurality of optical waveguide couplers; and processing a received signal resulting from light carried from the light source at each of the plurality of optical waveguide couplers to monitor a parameter based on the received signal.

According to yet another embodiment, an ocular insert includes a plurality of optical waveguide couplers, each optical waveguide coupler disposed at a respective location on the ocular insert, each optical waveguide coupler configured to emit a light received through a respective optical waveguide and receive a resulting signal.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 6 depicts processes involved in ocular monitoring according to embodiments.

DETAILED DESCRIPTION

Figure 1:
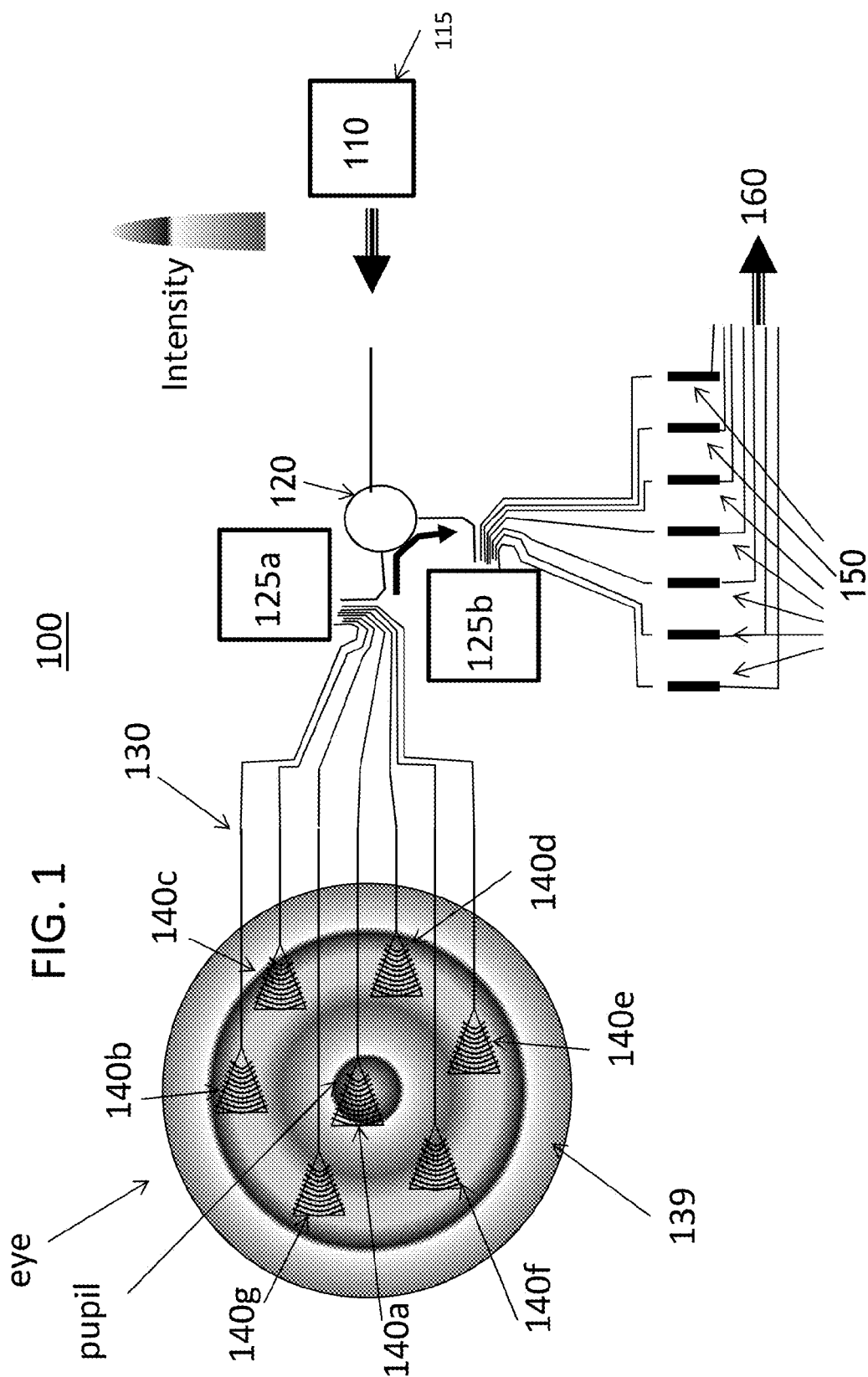
FIG. 1 depicts an ocular probing system according to an embodiment.

FIG. 1 depicts an ocular probing system 100 according to an embodiment. The system 100 includes a light source 110, a circulator 120, a pair of multiplexer/de-multiplexers 125a and 125b, a plurality of optical waveguides 130, a plurality of optical waveguide couplers 140 formed within an ocular insert 139, an array of detectors 150, and a processor 160. In the embodiment shown at FIG. 1, the light source 110 is a broadband light source 115 that may be selected from any available source of light with a spectrum of colors such as, for example, super-luminescent diodes (SLEDs), edge-emitting light emitting diodes (EELEDs), and the like. The light from the broadband light source 115 may be continuous or pulsed, as shown by FIG. 1. The circulator 120 functions to direct incoming broadband light to the multiplexer/de-multiplexer 125a, which separates (de-multiplexes) the colors of the light spectrum and directs each to a respective one of the optical waveguides 130. The multiplexer/de-multiplexer 125a may include, for example, an Echelle grating with each output slit width associated with the wavelength for one particular color of light. In alternate embodiments, the multiplexer/de-multiplexer 125a may be an arrayed waveguide grating (AWG). Each optical waveguide 130 or light wire carries one of the colors to a respective optical waveguide coupler 140 on the ocular insert 139 placed on the eye. In alternate embodiments, the multiplexer/de-multiplexer 125a may direct infrared light rather than light of different visible colors to the optical waveguide couplers 140. The optical waveguide 130 may be, for example, a standard channel waveguide, or, in alternate embodiments, a different waveguide structure, such as a slot waveguide, as discussed below. In alternate embodiments, the optical waveguide couplers 140 may be slot waveguides.

When the respective-colored light is directed to an optical waveguide coupler 140 spatially located at a particular part of the eye, the resulting received signal is directed back to the multiplexer/de-multiplexer 125a for multiplexing. The received signal may result from reflection of the emitted light or from a re-emission resulting from an optical process initiated by the emitted light. The circulator 120 passes this received signal to the multiplexer/de-multiplexer 125b so that the received signal corresponding to each color is separated and sent to a respective detector 150. The array of detectors 150 may be of any type, but compatibility with complementary metal-oxide-semiconductor (CMOS) circuits may result in a more cost-effective and easy to use system. In addition to being compatible with CMOS manufacturing methods, the ocular insert 139 may also be manufactured by other techniques such as, for example, as an optics stamp with a high-precision mold. In general, any suitable method of manufacture may be used to generate the ocular insert 139. In the exemplary CMOS-compatible system, the detectors 150 may be an array of charged couple devices (CCD) outputting a video signal. Alternately, the detector array may be germanium (Ge) based detectors, or an array of stand alone detector devices. The detectors 150 send their respective sensor signals to a processor 160. The processor 160 may be any digital signal processing device that receives the output of the detectors 150 and ultimately provides the desired information based on the signal received by the optical waveguide couplers 140. The processor 160 may receive an electrical signal related to the optical received signal of the optical waveguide couplers or may perform pre-processing on the optical received signal prior to signal processing.

In one embodiment, by knowing the spatial relationship of each optical waveguide coupler 140 with respect to the pupil as well as with respect to every other optical waveguide coupler 140, the processor 160 can use the relative received signal of different parts of the eye. This information may be used, for example, to monitor the level of dilation in the pupil of a comatose patient without the need to hold the patient's eye open periodically to conduct a test. In the case of monitoring pupil dilation, a reflection signal is received by each optical waveguide coupler 140. The difference in reflection between optical waveguide coupler(s) 140 at the center of the iris (e.g., 140*a* in FIG. 1) and optical waveguide couplers at outer regions of the eye (e.g., 140*d*) provides information about pupil dilation. In this way, real-time information may be obtained rather than information only during specified checks. The significance of shining light of a distinctive color at each optical waveguide coupler 140 is based on the predetermined spatial relationship between the optical waveguide couplers 140. That is, each color is associated with a particular location of the eye. Thus, the received reflection signal at each particular location of the eye is distinguished based on its color.

While the reflection signal at each optical waveguide coupler 140 needs to be distinguishable from that at every other optical waveguide coupler 140, the light exciting the eye itself could be an external light shined through a closed eyelid. That is, the light that causes the pupil to dilate does not have to be the light that is used to measure the pupil dilation. Thus, after an external light has been shone on the patient's eye (open or closed), the ocular probing system 100 may use the different wavelength light at each optical waveguide coupler 140 to distinguish the received reflection signal at each part of the eye to determine whether and how much the pupil has dilated. When the light at each optical waveguide coupler 140 is different from the light needed to stimulate the patient's eye, infrared light can also be supplied to each optical waveguide coupler 140 to generate a received reflection signal, rather than only visible light. For example, the multiplexer/de-multiplexer 125*a* may divide the incoming broadband light into different colors with infrared light being sent through an optical waveguide 130 to the optical waveguide coupler 140*a* located on the pupil. The resulting received reflection signal attributable to optical waveguide coupler 140*a* indicates the reflectivity and related information about the pupil. A received reflection signal may have an identifiable temporal or frequency signature or may have a temporal and frequency character nearly identical to the excitation light that resulted in the reflection.

Figure 2:
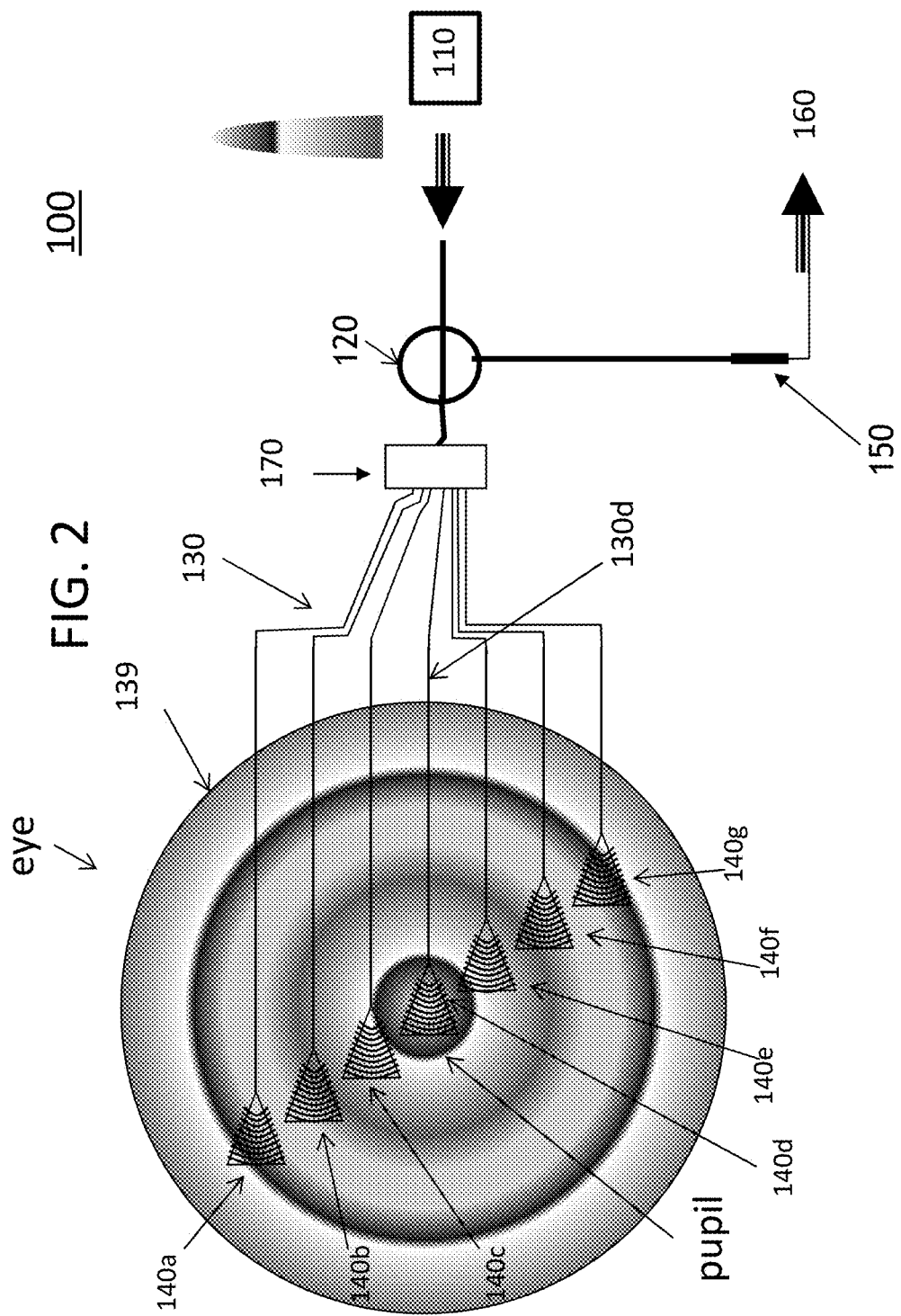
FIG. 2 depicts an ocular probing system according to another embodiment.

FIG. 2 depicts an ocular probing system 100 according to another embodiment. In this embodiment, path length to and from each optical waveguide coupler 140 is used for spatial resolution rather than color, as in the previous embodiment. That is, each different optical path length of optical waveguide 130 out of and into the power splitter 170 is associated with a particular location of the eye. Because color separation is not used for spatial resolution as in the previous embodiment, the light source 110 in the embodiment shown by FIG. 2 need not be a broadband light source 115, but may be a pulsed light source. In alternate embodiments, a single tunable laser line may be used as the light source 110 with the power splitter 170. In the embodiment shown by FIG. 2, the optical waveguide coupler 140*d* associated with the pupil corresponds with the optical waveguide 130*d*. Thus, the received signal received on the optical waveguide 130*d* indicates information about the pupil.

In any of the embodiments described with reference to FIG. 1 and FIG. 2 and additionally below, the optical waveguides 130 may be slotted optical waveguides rather than standard channel waveguides, as noted above. A slot waveguide optical waveguide 130 has a "slot" or "notch," usually along a section length, that concentrates the light in the notched region. When the light emitted through the slot is used as the excitation light, the resulting received signal can be collected by the slotted optical waveguide 140. The light concentrated in a slot is brighter than light emitted by a standard channel waveguide. As a result of the brighter light, the signal level of the received signal can be higher. Because the higher signal level is achieved without an increase in system noise sources, the signal-to-noise ratio of the received signal using an optical waveguide 130 that is a slot waveguide is generally higher.

Beyond monitoring reflectivity of different locations of the eye to determine responsiveness, for example, other conditions may be monitored with the above-described embodiments of the optical probe system. For example, by embedding a spectroscopic optical tag on a drug that is administered to a patient, an optical probe system according to embodiments described herein can be used to monitor the true dosage (absorption) in the patient. For example, the optical tag of a particular drug may be a material that absorbs light at one wavelength (color) and re-emits light at a different wavelength (color). In alternate embodiments, the optical tag may absorb light of one wavelength and re-emit light of the same or a different wavelength, but with a specific temporal decay signature. The amount of that re-emitted light that is received by the optical waveguide couplers 140 shown at FIG. 1 or FIG. 2 would indicate an amount of the drug. As noted above, in this embodiment, each optical waveguide coupler 140 receives a re-emitted signal rather than a reflection signal. When an optical response signature (as in the drug dosage monitoring example) is received and processed, rather than a reflection signal (as in the pupil dilation monitoring example), the process may be referred to as a "lab on a chip" process.

Figure 3:
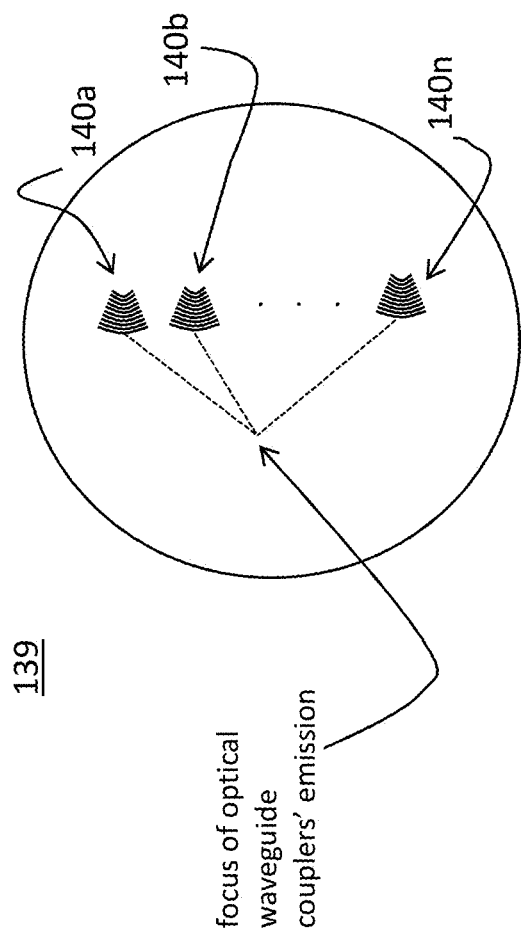
FIG. 3 depicts an exemplary arrangement of optical waveguide couplers on an ocular insert according to an embodiment of the optical probe system.

FIG. 3 depicts an exemplary arrangement of optical waveguide couplers 140 on an ocular insert 139 according to an embodiment of the optical probe system 100. In the embodiment shown by FIG. 3, the ocular insert 139 is an adaptive focus lens that allows ocular probing at different depths of the eye or in different directions on the eye. In this embodiment, the optical waveguide couplers 140 act in concert and the constructive interference among their individual signals is used for the directivity. In a radar system, phased array antennas are an array of antennas that are fed signals with their relative phases varied. The variation in phase results in facilitating directivity of the effective radiation pattern. In a somewhat similar manner, varying relative optical phase of the optical waveguide couplers 140 allows directivity. The specific distribution of the optical waveguide couplers 140 affects the nature of and degree of control over the directivity of the optical output. For example, a radial arrangement of the optical waveguide couplers 140 allows phase changes to direct their collective emission to different depths within the eye, while a linear arrangement of the optical waveguide couplers 140, as shown at FIG. 3, provides better side-to-side optical output control. With reference to the embodiment of FIG. 2, in which each optical waveguide coupler 140 has a different optical waveguide 130 path length, changing a wavelength of the input light changes the relative phase among the optical waveguide couplers 140.

Figure 4:
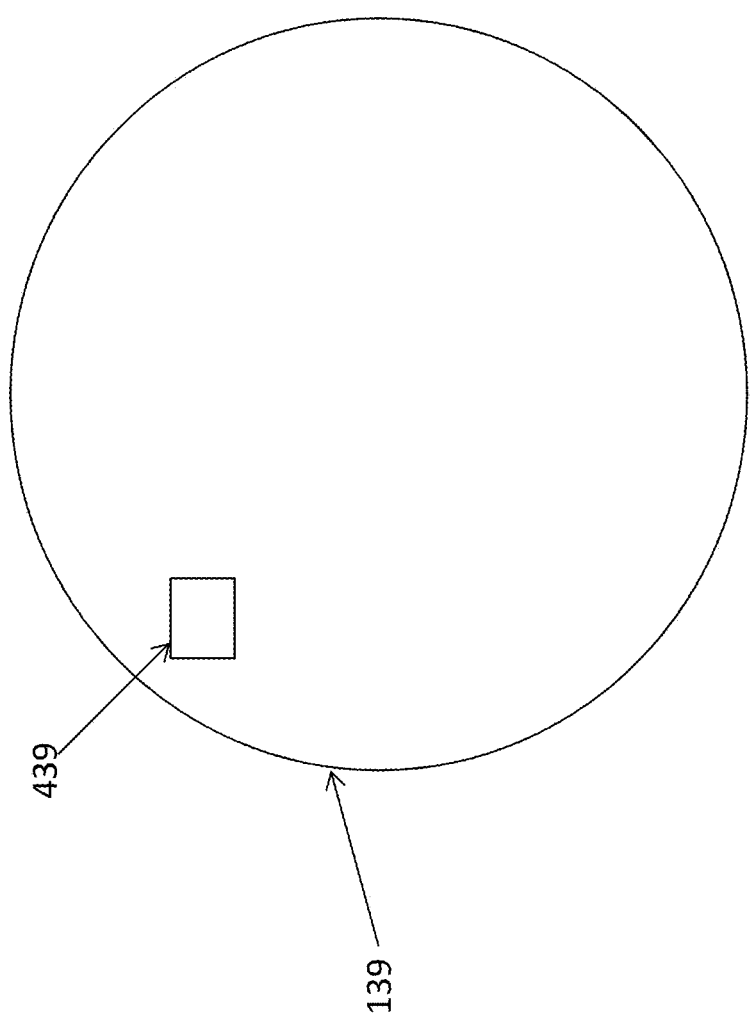
FIG. 4 depicts aspects of an ocular probing system according to yet another embodiment.

FIG. 4 depicts aspects of an ocular probing system 100 according to yet another embodiment. In the embodiment shown by FIG. 4, one or more mechanical devices 439 are part of the ocular insert 139. In alternate embodiments, the one or more mechanical devices 439 may monitor blood pressure, pulse, or other vital signs. An exemplary application of a mechanical device 439 is during surgery when a patient is under anesthesia. For example, complications such as blindness can sometimes result from lower back surgery. While the cause of the blindness is not fully understood, it is generally not directly attributed to the surgery but, instead, to a secondary effect such as pressure in the eye compounded by a patient's position during the surgery. By monitoring pressure in the patient's eye during surgery with a mechanical device 439, a change in position or some other adjustment may be made in time to prevent the blindness. The embodiment shown by FIG. 4 is readily combinable with any of the previously discussed embodiments. That is, for example, the ocular insert 139 may include the optical waveguide couplers 140 as well as one or more mechanical devices 439 discussed with reference to previous embodiments.

Figure 5:
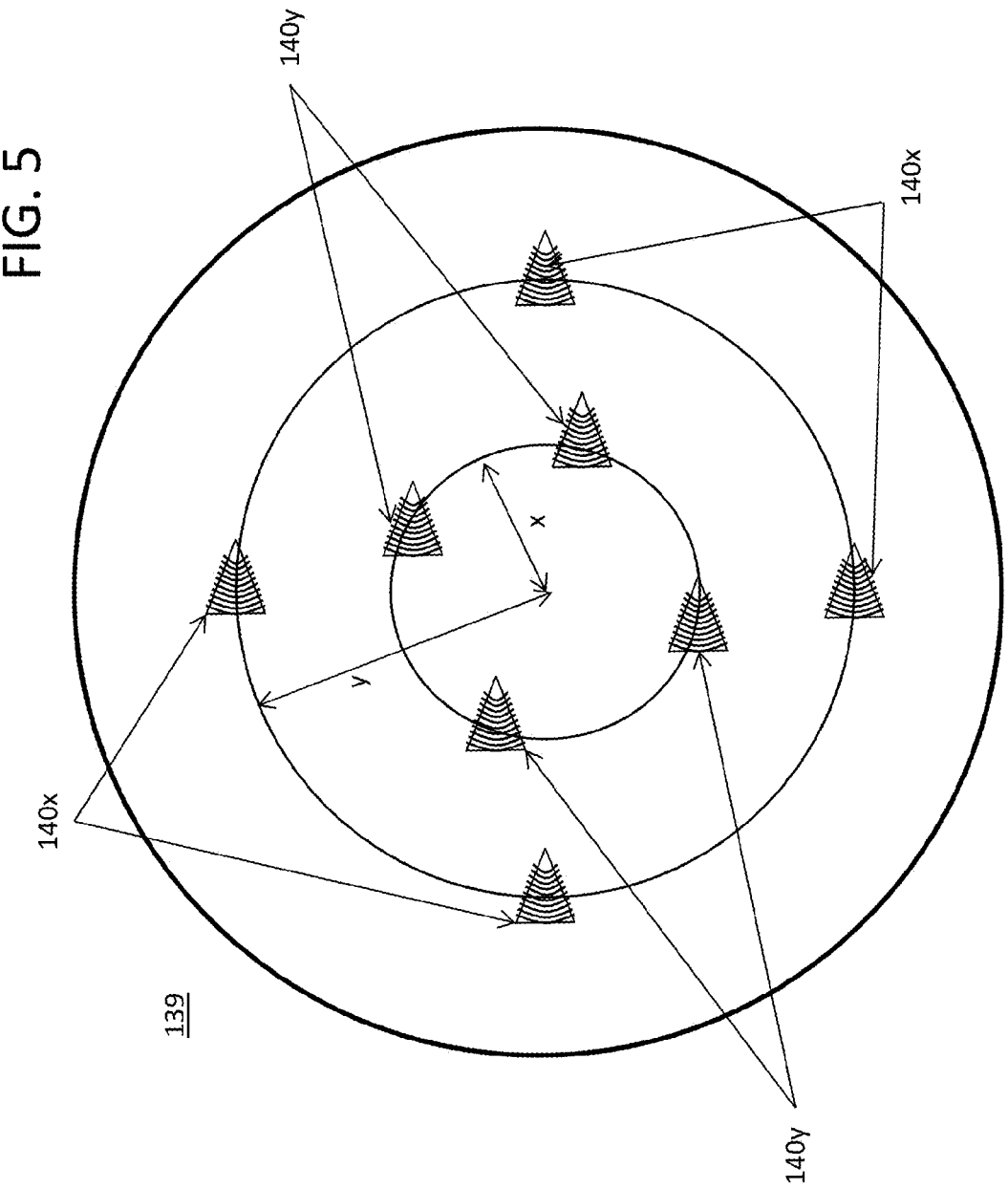
FIG. 5 depicts aspects of an ocular probing system according to yet another embodiment.

FIG. 5 depicts aspects of an ocular probing system 100 according to yet another embodiment. In the embodiment shown by FIG. 5, optical waveguide couplers 140 at equi-radial points are coupled into the same multiplexer/de-multiplexer 125 output. Thus, in the embodiment shown at FIG. 5, for example, the four optical waveguide couplers 140x at a radial distance x from a specified point on the ocular insert 139 (the center in the example shown by FIG. 5) couple into a 1×4 multi-mode interferometer (MMI) to have a common output into the multiplexer/de-multiplexer 125. The four optical waveguide couplers 140y at a radial distance y from the specified point on the ocular insert 139 are also coupled together. For example, the same color may be output from the multiplexer/de-multiplexer 125a (FIG. 1) to all four optical waveguide couplers 140x while a different color is output from the multiplexer/de-multiplexer 125a to all four optical waveguide couplers 140y. By using the same color (wavelength) for each equi-radial set of optical waveguide couplers 140, fewer wavelength channels (fewer colors) are needed to achieve the spatial differentiation needed to monitor pupil dilation, for example. With reference to one embodiment associated with FIG. 2, the power splitter 170 and single tunable laser line as the light source 110 may be used to tune the optical wavelength and change the relative phase between each set of optical waveguide couplers 140 (between optical waveguide couplers 140x and optical waveguide couplers 140y, for example). In this way, a phased array of light emitters is created as discussed with reference to FIG. 3. This optical wavelength tuning may be particularly useful, for example, in the drug dosage monitoring discussed above. The optical waveguide couplers 140 may be tuned to the wavelength emitted by the spectroscopic optical tags of the drugs of interest and the phased array of light emitters may be used to focus either or both the excitation and collected light.

FIG. 6 depicts processes involved in ocular monitoring according to embodiments. At block 610, the processes include disposing a plurality of optical waveguide couplers 140 on an ocular insert 139 as shown at FIGS. 1, 2, and 5, for example. As shown at block 620, the processes may further include disposing a mechanical device 439 on the ocular insert 139 as shown at FIG. 4, for example. As discussed with reference to FIG. 4, more than one mechanical device 439 may be included, and each mechanical device 439 may monitor a different vital sign such as blood pressure or pulse, for example. At block 630, the processes include providing a light source 110. The light source 110 may be, for example, a broadband light source as discussed with reference to FIG. 1 or a pulsed light source as discussed with reference to FIG. 2. As discussed above, the light source 110 may be different from a light source used to shine light on a patient's eye (with the lid open or closed) to stimulate pupil dilation, for example. As shown at block 640, the processes also include arranging optical waveguides 130, as shown at FIGS. 1 and 2, for example. The optical waveguides 130 carry light to the optical waveguide couplers 140. As discussed with reference to FIG. 1, the light carried to each optical waveguide coupler 140 may be of a different color (wavelength). Alternately, as discussed with reference to FIG. 2, light from a pulsed light source 110 may be carried by optical waveguides 130 of different optical path lengths to respective ones of the optical waveguide couplers 140. Light of the same color (wavelength) may be directed to all the optical waveguide couplers 140 that are at the same radial distance from a specified point on the ocular insert 139 as shown at block 650. The processes include carrying received signals (reflection or re-emission signals) from each of the optical waveguide couplers 140 at block 660 and, when equi-radial gratings 140 are provided with a same wavelength of light, the processes include coupling together the received signals from the equi-radial optical waveguide couplers 140 at block 670. The received signals are processed, as shown at block 680, to monitor physiological parameters such as pupil dilation, drug dosage and the like.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The flow diagrams depicted herein are just one example. There may be many variations to this diagram or the blocks (or operations) described therein without departing from the spirit of the invention. For instance, the blocks may be performed in a differing order or blocks may be added, deleted or modified. All of these variations are considered a part of the claimed invention.

While exemplary embodiments of the invention have been described, it will be understood that those skilled in the art, both now and in the future, may make various improvements and enhancements which fall within the scope of the claims which follow. These claims should be construed to maintain the proper protection for the invention first described.

What is claimed is:

1. A physiological monitoring system, comprising:
    a light source;
    a plurality of optical waveguide couplers, each of the plurality of optical waveguide couplers being arranged at a different predetermined spatial location on an ocular insert configured for placement on an eye;
    a plurality of optical waveguides, each optical waveguide configured to carry light from the light source to a respective one of the plurality of optical waveguide couplers and further configured to carry a received signal from the respective one of the plurality of optical waveguide couplers; and a processor configured to receive the received signal from each of the plurality of optical waveguides and to monitor a parameter based on associating the received signals from the plurality of optical waveguide couplers with a respective spatial location of the eye in relation to the different predetermined spatial location of the optical wave guide couplers.

2. The system according to claim 1, wherein a second light source is configured to shine visible light on the eye.

3. The system according to claim 1, wherein the received signal is a reflected signal resulting from a reflection of the light from the light source at each of the plurality of optical waveguide couplers.

4. The system according to claim 2, wherein the parameter is an amount of dilation of a pupil of the eye based on the received signal associated with the spatial location of the pupil of the eye.

5. The system according to claim 1, wherein the received signal is a re-emitted signal based on a process optically initiated by the light from the light source at each of the plurality of optical waveguide couplers.

6. The system according to claim 5, wherein the received signal has a signature frequency or temporal decay based on the optical process.

7. The system according to claim 6, wherein when a drug with an embedded spectroscopic optical tag is administered, the received signal is a re-emitted signal, and the parameter is an amount of drug absorption within the body.

8. The system according to claim 1, further comprising a circulator configured to direct the light from the light source to the plurality of optical waveguide couplers and to direct the received signal from each of the plurality of optical waveguide couplers to the processor.

9. The system according to claim 1, wherein the light source is a broadband light source and the system further comprises an Echelle grating configured to separate broadband light from the broadband light source into different colors, wherein each of the plurality of optical waveguides carries light of one of the different colors to a respective one of the plurality of optical waveguide couplers.

10. The system according to claim 9, wherein the spatial location of each of the plurality of optical waveguide couplers is determined based on the one of the different colors associated with each of the plurality of optical waveguide couplers.

11. The system according to claim 1, wherein the light source is a pulsed light, each of the plurality of optical waveguides has a different optical path length and is associated with a respective one of the plurality of optical waveguide couplers, and the spatial location of each of the plurality of optical waveguide couplers is determined based on the different optical path length associated with each of the plurality of optical waveguide couplers.

12. The system according to claim 1, wherein the plurality of optical waveguides is configured to carry infrared light to each of the plurality of optical waveguide couplers.

13. The system according to claim 1, wherein the plurality of optical waveguides are slotted waveguides such that each of the plurality of optical waveguides acts as a focusing element.

14. The system according to claim 1, wherein the plurality of optical waveguide couplers are slotted waveguides.

15. The system according to claim 1, further comprising at least one mechanical device arranged on the ocular insert and configured to determine at least one of blood pressure or pulse.

16. The system according to claim 1, wherein each of the plurality of optical waveguides carries light of a different wavelength to vary a relative optical phase among light provided to the plurality of optical waveguide couplers to adjust a depth of focus of emitted light from the plurality of optical waveguide couplers.

17. The system according to claim 1, wherein a relative optical phase of light provided to the plurality of optical waveguide couplers is varied to adjust a direction of focus of emitted light from the plurality of optical waveguide couplers.

18. The system according to claim 1, wherein light of a same optical wavelength is carried to equi-radial optical waveguide couplers among the plurality of optical waveguide couplers and received signals from the equi-radial optical waveguide couplers are coupled together.

* * * * *